United States Patent
Jameson et al.

(10) Patent No.: US 10,368,934 B2
(45) Date of Patent: Aug. 6, 2019

(54) ARRANGEMENT OF MULTI-CHANNEL BIPOLAR ELECTRODE ZONES TO MINIMIZE LEAKAGE AND EDGE EFFECTS

(71) Applicant: COVIDIEN LP, Mansfield, MA (US)

(72) Inventors: Allen D. Jameson, Sunnyvale, CA (US); Christopher L. Bagley, Santa Clara, CA (US); Hillary K. Huszar, Redwood City, CA (US)

(73) Assignee: COVIDIEN LP, Mansfield, MA (US)

( * ) Notice: Subject to any disclaimer, the term of this patent is extended or adjusted under 35 U.S.C. 154(b) by 736 days.

(21) Appl. No.: 14/919,218

(22) Filed: Oct. 21, 2015

(65) Prior Publication Data

US 2016/0199116 A1   Jul. 14, 2016

Related U.S. Application Data

(60) Provisional application No. 62/103,214, filed on Jan. 14, 2015.

(51) Int. Cl.
*A61B 18/00* (2006.01)
*A61B 18/14* (2006.01)

(52) U.S. Cl.
CPC .......... *A61B 18/00* (2013.01); *A61B 18/1492* (2013.01); *A61B 2018/0016* (2013.01);
(Continued)

(58) Field of Classification Search
CPC ............... A61B 18/00; A61B 18/1492; A61B 2018/0016; A61B 2018/00214;
(Continued)

(56) References Cited

U.S. PATENT DOCUMENTS

| 4,740,207 A | 4/1988 | Kreamer |
| 4,969,890 A | 11/1990 | Sugita |

(Continued)

FOREIGN PATENT DOCUMENTS

| DE | 102013104948 A1 | 11/2014 |
| EP | 1654980 A1 | 10/2006 |

(Continued)

OTHER PUBLICATIONS

Notification of the First Office Action from State Intellectual Property Office of the People's Republic of China for Application No. 201510845131.4 dated Aug. 21, 2017.

(Continued)

*Primary Examiner* — Ronald Hupczey, Jr.

(57) ABSTRACT

Methods, apparatuses, and systems are described for minimizing various leakage effects of multi-zone ablation devices. Apparatuses may include an ablation device for treatment of tissue including an ablation structure with a plurality of bipolar electrode zones. Each of the zones may include an in-zone channel pair comprising a positive channel and a negative channel. The ablation structure may be configured such that, for any adjacent electrode zone pair comprising a first electrode zone and a second electrode zone adjacent to the first electrode zone, the positive channel of the first electrode zone is electrically distinct from the positive channel of the second electrode zone, and the negative channel of the first electrode zone is electrically distinct from the negative channel of the second electrode zone. Moreover, the ablation structure may be arranged such that a total number of electrically distinct channels that is less than twice a total number of the plurality of electrode zones.

15 Claims, 7 Drawing Sheets

(52) U.S. Cl.
CPC .......... *A61B 2018/0022* (2013.01); *A61B 2018/00214* (2013.01); *A61B 2018/00577* (2013.01); *A61B 2018/00654* (2013.01); *A61B 2018/1465* (2013.01); *A61B 2018/1467* (2013.01)

(58) Field of Classification Search
CPC .. A61B 2018/0022; A61B 2018/00577; A61B 2018/00654; A61B 2018/1465; A61B 2018/1467
See application file for complete search history.

(56) References Cited

U.S. PATENT DOCUMENTS

| | | | |
|---|---|---|---|
| 4,998,539 A | 3/1991 | Delsanti | |
| 5,010,895 A | 4/1991 | Maurer et al. | |
| 5,192,297 A | 3/1993 | Hull | |
| 5,462,545 A | 10/1995 | Wang et al. | |
| 5,517,989 A | 5/1996 | Frisbie et al. | |
| 5,533,958 A | 7/1996 | Wilk | |
| 5,562,720 A * | 10/1996 | Stern ................. | A61B 18/1206 606/32 |
| 5,620,481 A * | 4/1997 | Desai ................ | A61B 18/1492 606/31 |
| 5,716,410 A | 2/1998 | Wang et al. | |
| 5,800,334 A | 9/1998 | Wilk | |
| 5,820,629 A | 10/1998 | Cox | |
| 5,836,874 A | 11/1998 | Swanson et al. | |
| 5,846,196 A | 12/1998 | Siekmeyer et al. | |
| 5,997,534 A | 12/1999 | Tu et al. | |
| 6,006,755 A | 12/1999 | Edwards | |
| 6,016,437 A | 1/2000 | Tu et al. | |
| 6,096,054 A | 8/2000 | Wyzgala et al. | |
| 6,102,908 A | 8/2000 | Tu et al. | |
| 6,123,703 A | 9/2000 | Tu et al. | |
| 6,123,718 A | 9/2000 | Tu et al. | |
| 6,152,899 A | 11/2000 | Farley | |
| 6,156,060 A | 12/2000 | Roy | |
| 6,162,184 A | 12/2000 | Swanson | |
| 6,162,237 A | 12/2000 | Chan | |
| 6,254,598 B1 | 7/2001 | Edwards et al. | |
| 6,258,118 B1 | 7/2001 | Baum et al. | |
| 6,551,310 B1 | 4/2003 | Ganz et al. | |
| 6,752,806 B2 | 6/2004 | Durgin et al. | |
| 6,800,083 B2 | 10/2004 | Hiblar et al. | |
| 6,964,661 B2 | 11/2005 | Rioux et al. | |
| 8,192,426 B2 | 6/2012 | Stern et al. | |
| 2002/0065542 A1 | 5/2002 | Lax | |
| 2003/0158550 A1 | 8/2003 | Ganz et al. | |
| 2005/0010209 A1* | 1/2005 | Lee, Jr. ............. | A61B 18/1206 606/41 |
| 2007/0276361 A1 | 11/2007 | Stevens-Wright et al. | |
| 2008/0249464 A1 | 10/2008 | Spencer et al. | |
| 2008/0319350 A1 | 12/2008 | Wallace | |
| 2009/0093802 A1 | 4/2009 | Kulesa | |
| 2014/0378966 A1 | 12/2014 | Haverkost | |
| 2014/0378967 A1 | 12/2014 | Willard | |
| 2015/0119879 A1 | 4/2015 | Jameson et al. | |
| 2015/0119880 A1 | 4/2015 | Huszar et al. | |
| 2015/0119881 A1 | 4/2015 | Bagley et al. | |

FOREIGN PATENT DOCUMENTS

| | | |
|---|---|---|
| EP | 2604212 A1 | 6/2013 |
| JP | 2014530644 | 11/2014 |
| WO | 0128446 A1 | 4/2001 |
| WO | 2005067668 A2 | 7/2005 |
| WO | 2008061528 A1 | 5/2008 |

OTHER PUBLICATIONS

Chinese Office action for Application No. 201610068875.4 dated Oct. 10, 2017, from the Chinese Patent Office.
Patent Examination Report No. 1 for Patent Application No. 2015249116, dated Oct. 20, 2016, from the Australian Government.
Office Action from the Canadian Intellectual Property Office dated Mar. 21, 2017 for Application No. 2,917,513.
Extended European Search report for Application No. 15202393.3 dated Jun. 22, 2016 from European Patent Office.
Extended EP Search Report for Application 15191980.0 from European Patent Office, dated Jun. 14, 2016.
Canadian Office Action for Canada Patent Application No. 2,910,361 dated Sep. 27, 2016, from the Canadian Intellectual Property Office.
Notice of Reasons for Rejection for Japanese Patent Application No. 2014-530644, dated Apr. 5, 2017, from the Japanese Patent Office.

* cited by examiner

ARRANGEMENT OF MULTI-CHANNEL BIPOLAR ELECTRODE ZONES TO MINIMIZE LEAKAGE AND EDGE EFFECTS

CROSS REFERENCE TO RELATED APPLICATION

The present application claims the benefit of and priority to U.S. Provisional Application Ser. No. 62/103,214, filed on Jan. 14, 2015, the entire contents of which are incorporated herein by reference.

BACKGROUND

The human body has a number of internal body lumens or cavities located within, such as the differing parts of the gastro-intestinal tract, many of which have an inner lining or layer. Body lumens may include, for example, the esophagus, small and large intestines, stomach, remnant after bariatric surgery, rectum and anus. These inner linings may be susceptible to disease. In some cases, different ablation techniques may be utilized with respect to the inner lining in order to prevent the spread of disease to otherwise healthy tissue located nearby.

Ablation devices may include multiple distinct areas or zones that may be selectively activated or deactivated during an ablation procedure. However, in certain circumstances, when a particular zone is activated, current may leak from that zone to one or more of the other zones of the ablation device. The problem of current leakage may result in insufficient energy being delivered to the intended zone, which may cause insufficient ablation of the target tissue.

Therefore, there may be a need for systems, devices and methods that may overcome the above or other disadvantages of known systems, devices, and methods.

SUMMARY

The described features generally relate to methods, systems, and devices for minimizing various leakage effects of multi-zone ablation devices. A device for treatment of tissue may include an ablation structure with a plurality of bipolar electrode zones. Each electrode zone may include a positive channel and a negative channel. According to various embodiments described herein, the channels and electrode zones may be arranged to reduce the current losses associated with in-zone and adjacent-zone leakage effects.

An ablation device for treatment of tissue is provided in accordance with various embodiments. The ablation device may include an ablation structure including a plurality of bipolar electrode zones. Each electrode zone may include an in-zone channel pair that comprises a positive channel and a negative channel. Furthermore, the ablation structure may be configured such that, for any adjacent electrode zone pair including a first electrode zone and a second electrode zone adjacent to the first electrode zone, the positive channel of the first electrode zone is electrically distinct from the positive channel of the second electrode zone, and the negative channel of the first electrode zone is electrically distinct from the negative channel of the second electrode zone. Moreover, the ablation structure comprises a total number of electrically distinct channels that is less than twice a total number of the plurality of electrode zones in various embodiments.

In certain embodiments, the ablation structure is further configured such that every shared-positive-channel electrode zone pair comprises a negative channel pair that is electrically distinct from the negative channel pair of every other shared-positive-channel electrode zone pair. According to some embodiments, the ablation structure is further configured such that every in-zone channel pair is electrically distinct from every adjacent-zone channel pair.

Moreover, the ablation structure is further configured such that each electrode zone comprises an in-zone channel pair that is electrically distinct from the in-zone channel pair of every other electrode zone in various embodiments.

According to some embodiments, each of the electrode zones are configured to be selectively enabled or disabled. For example, each of the electrode zones may be configured to be selectively enabled by supplying alternating current to the in-zone channel pair of each electrode zone. In various embodiments, the plurality of electrode zones of an ablation structure are aligned adjacent to each other. Furthermore, the plurality of electrode zones may be equal in width.

In various embodiments described, an ablation device may further include a catheter, an expansion member coupled with a distal portion of the catheter, an ablation structure support coupled with the ablation structure, wherein the ablation structure and the ablation structure support are configured to at least partially unfurl or furl around the expansion member as the expansion member expands or contracts.

In some embodiments, the expansion member is a balloon. The balloon may be made from a semi-compliant material in some embodiments.

In a particular embodiment, an ablation device comprises six electrode zones wherein a first electrode zone comprises an in-zone channel pair including a first positive channel and a first negative channel, a second electrode zone adjacent to the first electrode zone comprises an in-zone channel pair including a second positive channel and a second negative channel, and a third electrode zone adjacent to the second electrode zone comprises an in-zone channel pair including a third positive channel and a third negative channel. Additionally, a fourth electrode zone adjacent to the third electrode zone comprises an in-zone channel pair including the first positive channel and the second negative channel, a fifth electrode zone adjacent to the fourth electrode zone comprises an in-zone channel pair including the third positive channel and the first negative channel, and a sixth electrode zone adjacent to the fifth electrode zone comprises an in-zone channel pair including the second positive channel and the third negative channel.

In another particular embodiment described including six electrode zones, a first electrode zone comprises an in-zone channel pair including a first positive channel and a first negative channel, a second electrode zone adjacent to the first electrode zone comprises an in-zone channel pair including a second positive channel and a second negative channel, and a third electrode zone adjacent to the second electrode zone comprises an in-zone channel pair including a third positive channel and a third negative channel. Moreover, a fourth electrode zone adjacent to the third electrode zone comprises an in-zone channel pair including the first positive channel and the second negative channel, a fifth electrode zone adjacent to the fourth electrode zone comprises an in-zone channel pair comprising the second positive channel and the third negative channel, and a sixth electrode zone adjacent to the fifth electrode zone comprises an in-zone channel pair comprising the third positive channel and a fourth negative channel.

In yet another particular embodiment described, an ablation structure comprises seven electrode zones. According to various embodiments, a first electrode zone comprises an in-zone channel pair comprising a first positive channel and a first negative channel, a second electrode zone adjacent to the first electrode zone comprises an in-zone channel pair comprising a second positive channel and a second negative channel, a third electrode zone adjacent to the second electrode zone comprises an in-zone channel pair comprising a third positive channel and the first negative channel, and a fourth electrode zone adjacent to the third electrode zone comprises an in-zone channel pair comprising the second positive channel and a third negative channel. Moreover, a fifth electrode zone adjacent to the fourth electrode zone comprises an in-zone channel pair comprising a fourth positive channel and the first negative channel, a sixth electrode zone adjacent to the fifth electrode zone comprises an in-zone channel pair comprising a fifth positive channel and the second negative channel, and a seventh electrode zone adjacent to the sixth electrode zone comprises an in-zone channel pair comprising the first positive channel and the third negative channel.

In another particular embodiment of an ablation structure including seven electrode zones, a first electrode zone comprises an in-zone channel pair comprising a first positive channel and a first negative channel, a second electrode zone adjacent to the first electrode zone comprises an in-zone channel pair comprising a second positive channel and a second negative channel, a third electrode zone adjacent to the second electrode zone comprises an in-zone channel pair comprising a third positive channel and the first negative channel, and a fourth electrode zone adjacent to the third electrode zone comprises an in-zone channel pair comprising the second positive channel and a third negative channel. Additionally, a fifth electrode zone adjacent to the fourth electrode zone comprises an in-zone channel pair comprising a fourth positive channel and the first negative channel, a sixth electrode zone adjacent to the fifth electrode zone comprises an in-zone channel pair comprising a fifth positive channel and the third negative channel, and a seventh electrode zone adjacent to the sixth electrode zone comprises an in-zone channel pair comprising the fourth positive channel and the second negative channel.

According to various embodiments, a method of designing an ablation structure with multiple bipolar electrode zones for treating tissue is provided. The method may include providing each electrode zone with an in-zone channel pair comprising a positive channel and a negative channel, and limiting a total number of electrically distinct channels of the ablation structure such that the total number of electrically distinct channels is less than twice a total number of the plurality of electrode zones. Moreover, the method may also include arranging the positive channels of each electrode zone such that, the positive channel of any electrode zone is electrically distinct from the positive channel of any adjacent electrode zone and arranging the negative channels of each electrode zone such that the negative channel of any electrode zone is electrically distinct from the negative channel of any adjacent electrode zone.

In some embodiments, the method further comprises arranging the positive and negative channels of each electrode zone such that every shared-positive-channel electrode zone pair comprises a negative channel pair that is electrically distinct from the negative channel pair of every other shared-positive-channel electrode zone pair.

Moreover, in certain embodiments, the method further comprises arranging the positive and negative channels of each electrode zone such that every in-zone channel pair is electrically distinct from every adjacent-zone channel pair.

Certain embodiments of the present disclosure may include some, all, or none of the above advantages or features. One or more other technical advantages or features may be readily apparent to those skilled in the art from the figures, descriptions, and claims included herein. Moreover, while specific advantages or features have been enumerated above, various embodiments may include all, some, or none of the enumerated advantages or features.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

To treat certain conditions within a body lumen, such as the gastrointestinal tract, area-based ablation may be used to ablate specific segments of tissue. For various reasons, an area-based ablation device may be divided into multiple distinct areas or zones that are selectively operable. One such reason for dividing an area-based ablation device into multiple zones may be to maintain a high degree of control over which areas of tissue are being ablated at any given time during an ablation procedure. Another reason is that a typical power supply may not be capable of providing sufficient energy to the entire ablation structure simultaneously. However, in certain circumstances, current from an activated zone may leak or travel along an alternate path to one or more of the other zones of the ablation device. The problem of current leakage may be the result of the physical arrangement and proximity of the different zones with respect to each other, or the arrangement and number of electrically distinct electrical channels that power the zones, or some combination of both. In any case, this leakage may reduce the amount of energy delivered to the target zone, which may result in insufficient ablation of the target tissue.

As described herein, a distinct area or zone of an area-based ablation device capable of ablating a corresponding area of tissue is referred to as an electrode zone. In accordance with various embodiments, each of the multiple electrode zones of an area-based ablation device may be powered by one or more electrical channels. As used herein, a channel is an electrical connection which may be activated or deactivated by selectively supplying current from a power source. For example, a channel may be an individual wire connecting an electrode zone to a power source. In some embodiments, the electrode zones of an ablation device are bipolar electrode zones comprising two electrical channels each. Therefore, if each electrode zone comprised two electrically distinct channels, then the total number of electrically distinct channels would be twice the number of electrode zones.

However, in accordance with various embodiments described herein, the total number of distinct electrical channels may be reduced to less than twice the total number of electrode zones of an ablation device. For example, instead of ten distinct electrical channels, a five-zone ablation device may have nine or eight or even fewer distinct electrical channels. Reducing the number of distinct electrical channels of an ablation device may advantageously reduce the size and manufacturing cost of the ablation device. However, if an ablation device has a total number of distinct electrical channels that is less than twice the total number of electrode zones, then the device may be susceptible to various leakage and edge effects. As used herein, leakage effects refers to the delivery of power outside of the intended treatment area or zone, which decreases the power delivered to the intended treatment area or zone. Edge effects refers to the phenomena which change the behavior of energy delivery on the peripheries of electrode zones, whether or not adjacent to another electrode zone. Therefore, in accordance with various embodiments described herein, the electrical channels of a multi-zone ablation device may be arranged and configured so as to reduce potential leakage effects, edge effects, or any combination of the two.

Figure 1A:
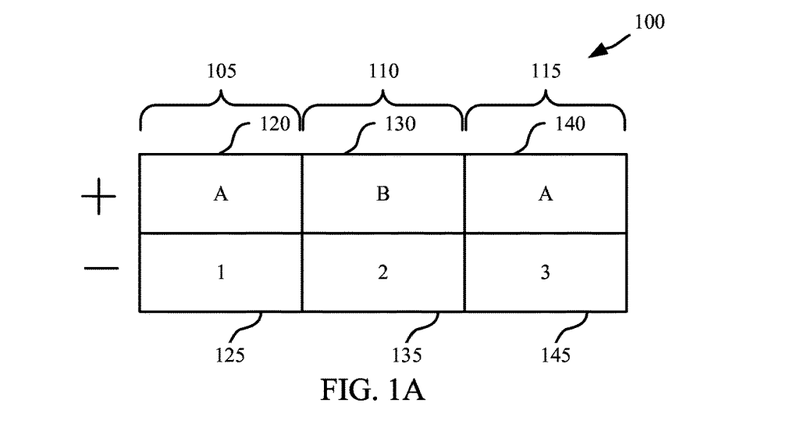
FIG. 1A is a schematic diagram of an ablation structure with three electrode zones in accordance with various embodiments.

Referring to FIG. 1A, a schematic diagram of an ablation structure 100 is shown in accordance with various embodiments. The ablation structure 100 is illustrated with three electrode zones, 105, 110, and 115. Each of the electrode zones 105, 110, 115 are examples of bipolar electrode zones. Accordingly, each electrode zone 105, 110, 115 comprises two electrical channels. For example, zone 105 comprises channels 120 and 125, zone 110 comprises channels 130 and 135, and zone 115 comprises channels 140 and 145. The two channels of each electrode zone may be referred to as a "positive channel" and a "negative channel." However, in certain embodiments, the energy delivered to the ablation structure is non-grounded alternating current (AC) power. In such embodiments, the positive and negative channels of each electrode zone are functionally equivalent. Nevertheless, for labeling purposes, one channel of a bipolar electrode zone is referred to as the positive channel and the other channel is referred to as the negative channel. As used with reference to the figures described herein, the positive channels are labeled with letters (e.g., A, B, C) and the negative channels are labeled with numbers (1, 2, 3).

At this point, it is important to distinguish between the labeling conventions of the numeric identifiers of the channels (e.g., 120 and 125) and the names of the channels (e.g., A and 1). As used herein, a channel name (e.g., A) denotes a channel that is electrically distinct from all other channels with a different name on the ablation device. For example the positive channel A is electrically distinct from the positive channel B, and both channels A and B are electrically distinct from negative channel 1. An electrically distinct channel means that the channel is not directly electrically connected to any of the other channels. For example channel A and channel B may be completely separate wires. On the other hand, the numeric identifiers, such as 120 and 125, merely denote the schematic location of a particular channel within a particular electrode zone. As shown in FIG. 1A, two channels with different numeric identifiers may or may not be electrically distinct. For example, channel 120 of electrode zone 105 and channel 140 of electrode zone 115 are both labeled A, which means they are the same electrical channel and are therefore not electrically distinct. However, channel 120 of electrode zone 105 and channel 130 of electrode zone 110 are labeled A and B respectively, which means that they are electrically distinct channels.

For ease of reference, as used herein, the combination of two electrical channels may be referred to as a "channel pair." For example, the combination of the positive and negative channel of an electrode zone is referred to as an "in-zone channel pair." With reference to FIG. 1A, the in-zone channel pair of electrode zone 105 is "A1," and the in-zone channel pair of electrode zone 110 is "B2." Similar to an in-zone channel pair, an "adjacent-zone channel pair" includes one positive channel and one negative channel. However, an adjacent-zone channel pair includes the positive channel of one zone and the negative channel of an adjacent zone. For example, referring to FIG. 1A, an adjacent-zone channel pair between electrode zones 105 and 110 is channel pair A2 (i.e., the positive channel of electrode zone 105 and the negative channel of electrode zone 110). Furthermore, the other adjacent-zone channel pair between electrode zones 105 and 110 is channel pair B1 (i.e., the positive channel of electrode zone 110 and the negative channel of electrode zone 105). It may be appreciated that any two electrode zones that are adjacent to each other comprise two adjacent-zone channel pairs.

In a similar manner, the combination of two electrode zones may be referred to as an "electrode zone pair" for ease of reference. For example, as used herein, an "adjacent electrode zone pair," refers to any two electrode zones of an ablation device that are located adjacent to each other. For example, with reference to FIG. 1A, electrode zones 105 and 110 make up an adjacent electrode zone pair referred to as A1/B2. Furthermore, electrode zones 110 and 115 make up a different adjacent electrode zone pair referred to as B2/A3. It may be appreciated that for any ablation structure with N number of electrode zones, there are N−1 different adjacent electrode zone pairs. Moreover, as used herein, a "shared-positive-channel electrode zone pair" comprises any two electrode zones that share a positive channel whether the two electrode zones are adjacent to each other or not. For example, with reference to FIG. 1A, electrode zones 105 and 115 both share the positive channel A. Therefore, electrode zones 105 and 115 make up a shared-positive-channel electrode zone pair referred to as A1/A3. The two negative channels associated with the A1/A3 electrode zone pair may be referred to as a "negative channel pair." With reference to FIG. 1A, the negative channel pair of the shared-positive-channel electrode zone pair A1/A3 is 1/3.

As described above, it may be advantageous to minimize the number of electrically distinct channels on an ablation structure for a given number of electrode zones. Therefore, according to various embodiments, an ablation structure comprises a total number of electrically distinct channels that is less than twice the total number of electrode zones. For example, with reference to FIG. 1A, the ablation structure 100 comprises three electrode zones (i.e., 105, 110, 115) and only five electrically distinct channels (i.e., A, B, 1, 2, and 3). However, unless the electrical channels are properly arranged, an ablation structure with a total number of electrically distinct channels that is less than twice the number of electrode zones may suffer from various leakage or edge effects.

Figure 1B:
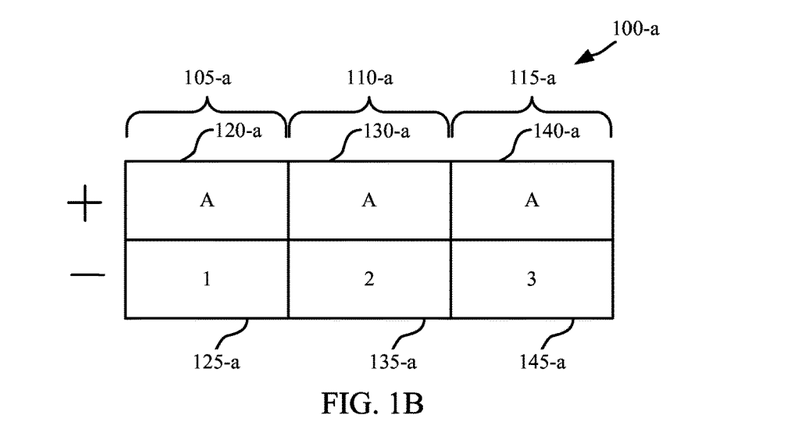
FIG. 1B is a schematic diagram of an ablation structure with three electrode zones in accordance with various embodiments.

To illustrate a potential leakage effect, consider ablation structure 100-a illustrated in FIG. 1B, which may be an alternate arrangement of ablation structure 100. The only difference between ablation structures 100 and 100-a is that channel 130-a is channel A instead of channel B. In this alternate arrangement, if electrode zone 105-a was activated (i.e., by activating channels 120-a and 125-a), then current may leak from channel 125-a (i.e., channel 1) to channel 130-a (i.e., channel A). This type of leakage may be referred to as an adjacent-zone alternate path because some of the current intended to travel between two in-zone channels has leaked to an adjacent zone. This leakage effect may result in an insufficient amount of energy being delivered to electrode zone 105-a to achieve ablation of the target tissue in contact with electrode zone 105-a.

Therefore, according to various embodiments, an ablation structure may be arranged such that for any adjacent electrode zone pair comprising a first electrode zone and a second electrode zone adjacent to the first electrode zone, the positive channel of the first electrode zone is electrically distinct from the positive channel of the second electrode zone and the negative channel of the first electrode zone is electrically distinct from the negative channel of the second electrode zone. Ablation device 100 shown in FIG. 1A illustrates an example of an ablation structure according to such an arrangement. For example, referring to the adjacent electrode zone pair A1/B2 (i.e., electrode zones 105 and 110), the positive channel of electrode zone 105 (i.e., channel A), is electrically distinct from the positive channel of the adjacent electrode zone 110 (i.e., channel B). Similarly, the negative channel of electrode zone 105 (i.e., channel 1) is electrically distinct from the negative channel of the adjacent electrode zone 110 (i.e., channel 2). The adjacent electrode zone pair B2/A3 (i.e., electrode zones 110 and 115) is also arranged such that the positive channel of the first electrode zone is electrically distinct from the positive channel of the adjacent electrode zone and the negative channel of the first electrode zone is electrically distinct from the negative channel of the adjacent electrode zone. Although the ablation structure 100 includes three electrode zones, the method of arrangement just described may be applied to an ablation device with any number of electrode zones.

Figure 2:
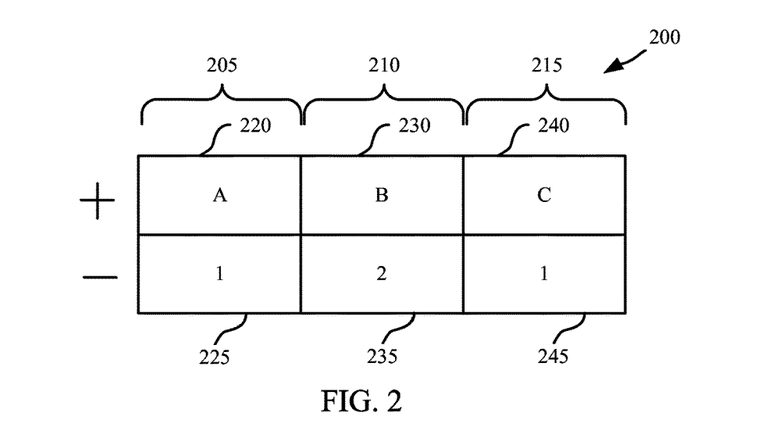
FIG. 2 is a schematic diagram of an ablation structure with three electrode zones in accordance with various embodiments.

With reference now to FIG. 2, an ablation structure 200 is schematically illustrated in accordance with various embodiments. Similar to ablation structure 100 of FIG. 1, the ablation structure 200 comprises three electrode zones 205, 210, and 215, where each zone comprises a positive channel and a negative channel. Also similar to ablation structure 100, the ablation structure 200 comprises a total of five electrically distinct channels. Moreover, similar to ablation structure 100, the ablation structure 200 is arranged such that for any adjacent electrode zone pair, the positive channel of the first electrode zone is electrically distinct from the positive channel of the adjacent electrode zone and the negative channel of the first electrode zone is electrically distinct from the negative channel of the adjacent electrode zone. However, unlike ablation structure 100, the ablation structure 200 comprises three electrically distinct positive channels (i.e., A, B, C), and only two electrically distinct negative channels (i.e., 1, 2).

Ablation structure 200 is a mirror image of the ablation structure 100 in that the only difference between the two is that the positive and negative electrodes are transposed. Therefore, in embodiments where the energy delivered to the electrode zones is non-grounded AC power, the ablation structures 100 and 200 are functionally equivalent. The ablation structures 100 and 200 illustrate a principal in accordance with various embodiments described herein that merely mirroring an ablation structure design by switching the positive and negative electrodes does not constitute a different electrode design.

Figure 3:
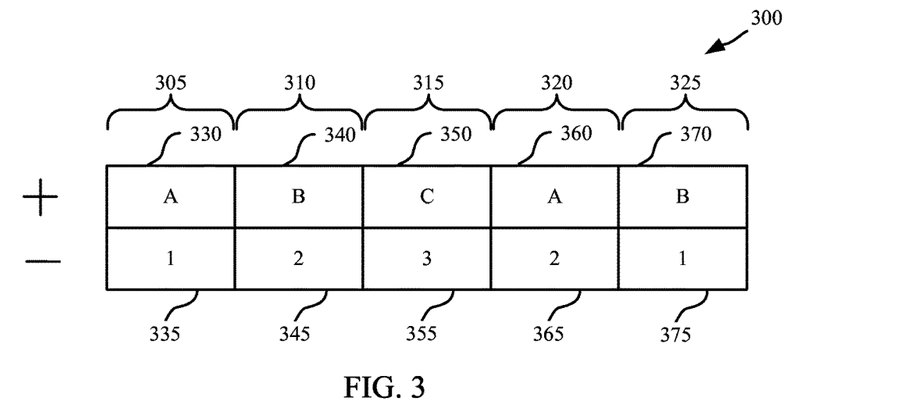
FIG. 3 is a schematic diagram of an ablation structure with five electrode zones in accordance with various embodiments.

With reference now to FIG. 3, an ablation structure 300 is schematically illustrated in accordance with various embodiments. Ablation structure 300 may be an example of the ablation structures 100 or 200 described with reference to FIGS. 1 and 2. In particular, the ablation structure 300 includes a total number of electrically distinct channels that is less than twice the total number of electrode zones. In particular, the ablation structure 300 includes five electrode zones 305, 310, 315, 320, 325 and a total of six electrically distinct channels, three of which are positive (i.e., A, B, and C), and three of which are negative, (i.e., 1, 2, and 3). Similar to the ablation structures 100 and 200, the ablation structure 300 is configured such that for any adjacent electrode zone pair comprising a first electrode zone and a second electrode zone adjacent to the first electrode zone, the positive channel of the first electrode zone is electrically distinct from the positive channel of the second electrode zone and the negative channel of the first electrode zone is electrically distinct from the negative channel of the second electrode zone.

However, as arranged, ablation structure 300 may suffer from various leakage effects. For example, if electrode zone 305 is activated (by activating channels A and 1), ideally all of the current would travel between channels 330 and 335 such that the target tissue in contact with zone 305 is fully ablated as intended. However, as arranged, current may travel between channels A and 1 along an alternate path other than the intended path between channels 330 and 335. As a result of this alternate path, current intended for electrode zone 305 may leak and be lost into one or more different electrode zones. To illustrate, as channels A and 1 are activated (i.e., to activate electrode zone 305), some of the current may leak from channel 360 (i.e., channel A) of electrode zone 320 to channel 365 (i.e., channel 2) of electrode zone 320, and then from channel 345 (i.e., channel 2) of electrode zone 310 to channel 340 (i.e., channel B) of electrode zone 310, and then further from channel 370 (i.e., channel B) of electrode zone 325 to channel 375 (i.e., channel 1) of electrode zone 325. Thus, the current intended to travel between channels A and 1 (i.e., through channels 330 and 335) is effectively split up into two different paths (i.e., the intended path and the alternate path), thereby reducing the amount of current traveling along the intended path. In this illustration, some of the current intended for electrode zone 305 is leaked into electrode zones 310, 320, and 325. This type of alternate path is referred to as an in-zone alternate path because the current is leaking between the in-zone channel pairs of an electrode zone as opposed to leaking between the adjacent-zone channel pairs of two adjacent electrode zones.

This example of an in-zone alternate path may be said to have three in-zone steps or hops. The first step is from channel 360 to channel 365; the second step is from channel 345 to channel 340, and the third step is from channel 370 to channel 375. It may be appreciated that the amount of current leakage depends on the total resistance of this alternate path compared to the resistance of the intended path. Thus, if the channels of the electrode zones are arranged such that the total resistance of any alternate path is sufficiently greater than the resistance of the intended path, then the amount of current leakage may be negligible. Therefore, in accordance with various embodiments, the channels of the electrode zones may be arranged to increase the total number of in-zone hops of potential alternate paths, thereby increasing the total resistance of the alternate paths.

Figure 4:
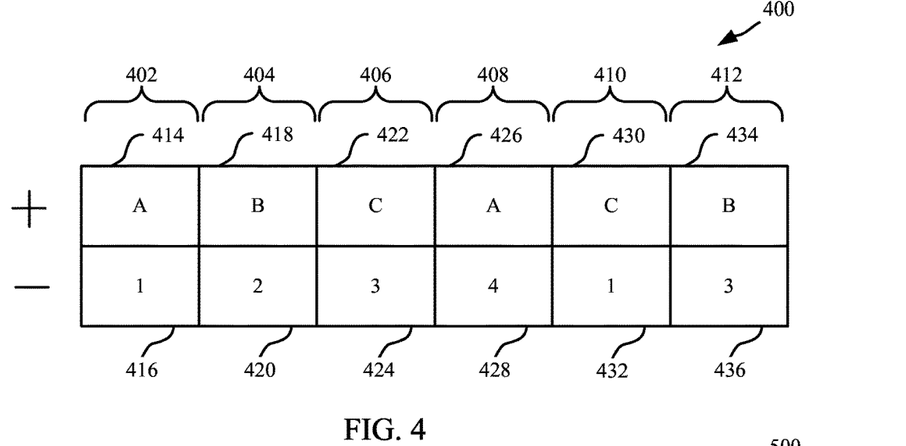
FIG. 4 is a schematic diagram of an ablation structure with six electrode zones in accordance with various embodiments.

For example, referring to FIG. 4, a schematic illustration of an ablation structure 400 is shown in accordance with various embodiments. Ablation structure 400 includes six electrode zones and a total of seven electrically distinct channels, three of which are positive (i.e., A, B, and C), and four of which are negative (i.e., 1, 2, 3, and 4). Therefore, similar to the ablation structures 100, 200, and 300, the ablation structure 400 includes a total number of electrically distinct channels that is less than twice the total number of electrode zones. Ablation structure 400 is also arranged similar to the ablation structures 100, 200 and 300 in that for any adjacent electrode zone pair comprising a first electrode zone and a second electrode zone adjacent to the first electrode zone, the positive channel of the first electrode zone is electrically distinct from the positive channel of the second electrode zone and the negative channel of the first electrode zone is electrically distinct from the negative channel of the second electrode zone.

However, to reduce potential problems associated with in-zone alternate path leakage effects described with reference to FIG. 3, the ablation structure 400 is further arranged such that every shared-positive-channel electrode zone pair comprises a negative channel pair that is electrically distinct from the negative channel pair of every other shared-positive-channel electrode zone pair. To illustrate, consider the three separate shared-positive-channel electrode zone pairs and their corresponding negative channel pairs with reference to FIG. 4. As shown, the shared-positive-channel electrode zone pair A1/A4 (i.e., electrode zones 402 and 408) includes the negative channel pair 1/4 (i.e., channels 416 and 428). Furthermore, the shared-positive-channel electrode zone pair B2/B3 (i.e., electrode zones 404 and 412) includes the negative channel pair 2/3. Lastly, the shared-positive-channel electrode zone pair C3/C1 (i.e., electrode zones 406 and 410) includes the negative channel pair 3/1. Therefore, as arranged on the ablation structure 400, each of the shared-positive-channel electrode zone pairs (i.e., A1/A4, B2/B3, and C3/C1) each include an electrically distinct negative channel pair (i.e., 1/4, 2/3, and 3/1). An electrically distinct negative channel pair refers to a channel pair that does not comprise the same two negative channels. According to this arrangement, although there may still be alternate in-zone current paths, the paths include more than three hops. Therefore, the total resistance of the alternate paths may be sufficiently high such that the current leakage due to in-zone alternate paths is negligible.

Although the ablation structure 400 is depicted with six electrode zones, it may be appreciated that the method of arrangement just described may be employed with any ablation structure with at least four electrode zones. Moreover, it may be appreciated that the arrangement described with reference to FIG. 4 may be combined with the arrangement as described with reference to FIGS. 1-3 or the arrangement may be employed alone. For example, as illustrated, ablation structure 400 is arranged such that for any adjacent electrode zone pair comprising a first electrode zone and a second electrode zone adjacent to the first electrode zone, the positive channel of the first electrode zone is electrically distinct from the positive channel of the second electrode zone and the negative channel of the first electrode zone is electrically distinct from the negative channel of the second electrode zone, and is further arranged such that every shared-positive-channel electrode zone pair comprises a negative channel pair that is electrically distinct from the negative channel pair of every other shared-positive-channel electrode zone pair. However, it may be appreciated that an ablation structure may be arranged such that every shared-positive-channel electrode zone pair comprises a negative channel pair that is electrically distinct from the negative channel pair of every other shared-positive-channel electrode zone pair, but for at least one adjacent electrode zone pair, either the positive or negative channel between the zone pair is shared.

Although the arrangement of the channels and electrode zones described with reference to FIG. 4 may reduce the leakage effect due to pure in-zone current leakage, in some scenarios, the adjacent-zone alternate path leakage problem described with reference to FIG. 1 and the in-zone alternate path leakage problem described with reference to FIG. 3 may combine to create other potential current leakage problems. For example, with reference to FIG. 4, by activating electrical channels 414 and 416 of electrode zone 402 (i.e., by activating channels A and 1), some current may travel from electrical channel 426 (i.e., channel A) of electrode zone 408 to electrical channel 432 (i.e., channel 1) of the adjacent electrode zone 410, thereby reducing the amount of current traveling between the intended electrode channels (e.g., channels 414 and 416).

Figure 5:
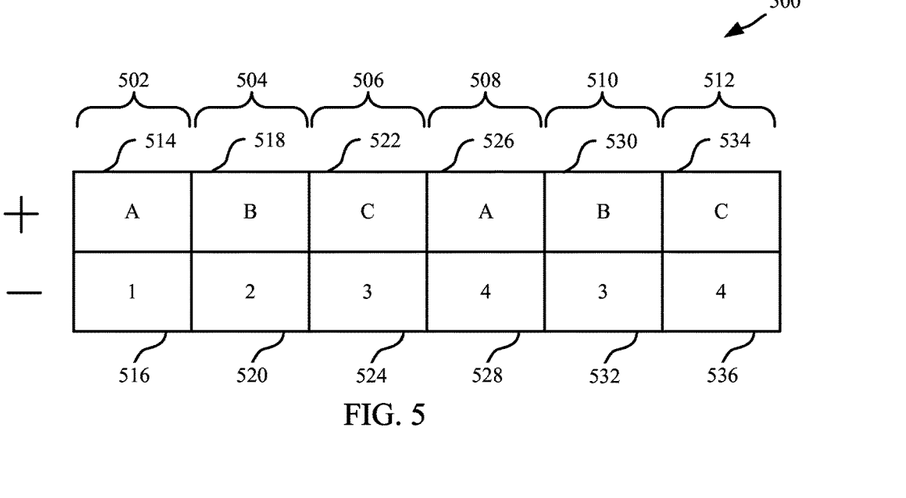
FIG. 5 is a schematic diagram of an ablation structure with six electrode zones in accordance with various embodiments.

Therefore, in accordance with various embodiments, an ablation structure may be arranged to reduce or eliminate this combination leakage effect for some or all of the electrode zones of an ablation structure. For example, referring to FIG. 5, a schematic diagram of an ablation structure 500 is illustrated in accordance with various embodiments. Ablation structure 500 may be an example of ablation structure 400. In fact, ablation structure 500 comprises the same number of electrical zones and electrically distinct positive and negative channels as ablation structure 400. However, ablation structure 500 is arranged such that the combination leakage effects for the first electrode zone (i.e., electrode zone 502) is reduced or eliminated. For example, referring to the in-zone channel pair of electrode zone 502 (i.e., channel pair A1), the ablation structure 500 is arranged such that there are no A1 adjacent-zone channel pairs. Thus, if electrode zone 502 is activated (i.e., by activating channels A and 1), there will be no combination adjacent-zone channel pair leakage effects. The same applies to electrode zone 504 because there are no adjacent zone channel pairs that are the same as the in-zone channel pair of electrode zone 504 (i.e., channel pair B2). However, notice that the same does not apply to electrode zone 506. As arranged, if electrode zone 506 were to be activated (i.e., by activating channels C and 3), there may be an adjacent zone leakage effect between channel 534 (i.e., channel C) of electrode zone 512 and channel 532 (i.e., channel 3) of electrode zone 510. Therefore, according to various embodiments, an ablation structure may be arranged such that for at least some of the electrode zones, the in-zone channel pair of those electrode zones are electrically distinct from every adjacent-zone channel pair. Although the ablation structure 500 is shown with six electrode zones, the method of arrangement just described may be employed with an ablation structure with any number of electrode zones.

Figure 6:
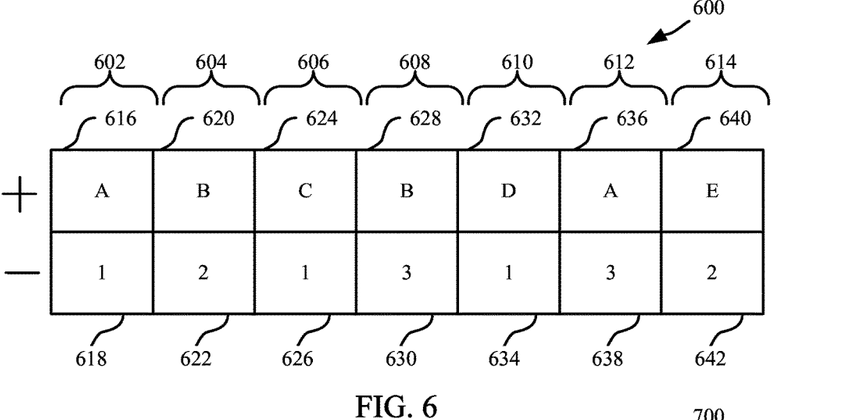
FIG. 6 is a schematic diagram of an ablation structure with seven electrode zones in accordance with various embodiments.

As another example, with reference to FIG. 6, a schematic diagram of an ablation structure 600 with seven electrode zones is shown in accordance with various embodiments. Ablation structure 600 may be an example of ablation structures 100, 200, 300, 400, or 500 described with reference to FIGS. 1-5. Accordingly, the ablation structure 600 includes a total number of electrically distinct channels that is less than twice a total number of electrode zones. Specifically, the ablation structure 600 includes seven electrode zones and a total of eight electrically distinct channels, of which five are positive (i.e., A, B, C, D, and E), and three are negative (i.e., 1, 2, and 3). Moreover, ablation structure 600 is arranged similar to the ablation structures 100, 200, 300, 400, or 500 in that ablation structure 600 is configured such that for any adjacent electrode zone pair comprising a first electrode zone and a second electrode zone adjacent to the first electrode zone, the positive channel of the first electrode zone is electrically distinct from the positive channel of the second electrode zone and the negative channel of the first electrode zone is electrically distinct from the negative channel of the second electrode zone. Additionally, the ablation structure 600 may be an example of the ablation structures 400 and 500 in that the ablation structure 600 is further arranged such that every shared-positive-channel electrode zone pair comprises a negative channel pair that is electrically distinct from the negative channel pair of every other shared-positive-channel electrode zone pair.

However, similar to the ablation structure 500, the ablation structure 600 is arranged such that for at least one of the electrode zones, there are alternate paths due to the combination adjacent-zone leakage effects. For example consider electrode zone 602, which comprises an in-zone channel pair A1. If electrode zone 602 is activated by activating channels A and 1, there may be adjacent zone leakage from channel 636 (i.e., channel A) of electrode zone 612 to channel 634 (i.e., channel 1) of electrode zone 610. Even though there may be leakage effects due to activating zone 602, because the in-zone channel pairs of the other electrode zones (i.e., zones 604, 608, 610, 612, and 614), are electrically distinct from all the adjacent-zone channel pairs, activation of these electrode zones will not result in the combination adjacent-zone leakage effects. Although the ablation structure 600 is shown with seven electrode zones, it may be appreciated that the method of arrangement just described may be employed with an ablation structure with any number of electrode zones.

Figure 7:
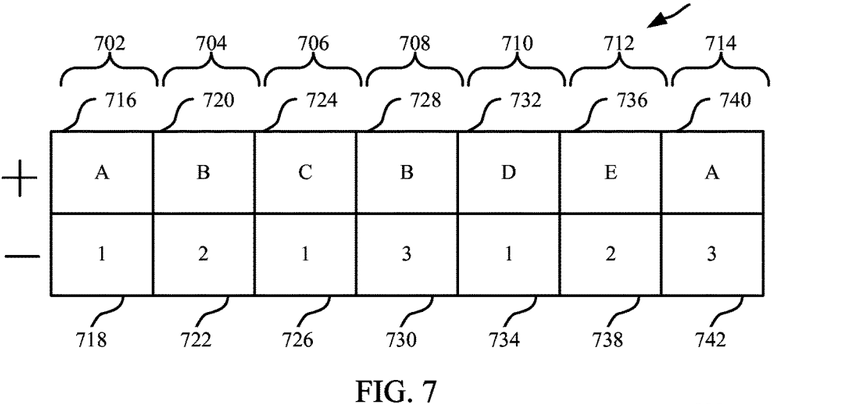
FIG. 7 is a schematic diagram of an ablation structure with seven electrode zones in accordance with various embodiments.

In accordance with various embodiments, an ablation structure may be arranged to reduce or eliminate the combination adjacent-zone leakage effects for all of the electrode zones. With reference to FIG. 7, a schematic diagram of an ablation structure 700 with seven electrode zones is shown in accordance with various embodiments. Ablation structure 700 is nearly identical to the ablation structure 600, except that the last two electrode zones (i.e., zones 712 and 714) are transposed from their arrangement shown in the ablation structure 600. Accordingly, the ablation structure 700 is an example of an ablation structure arranged such that every in-zone channel pair is electrically distinct from every adjacent-zone channel pair. To illustrate, notice how every possible adjacent-zone channel pair (i.e., A2, B1, C2, C3, D3, E1, D2, E3, and A2) is electrically distinct from every in-zone channel pair (i.e., A1, B2, C1, B3, D1, E2, and A3).

Figure 8:
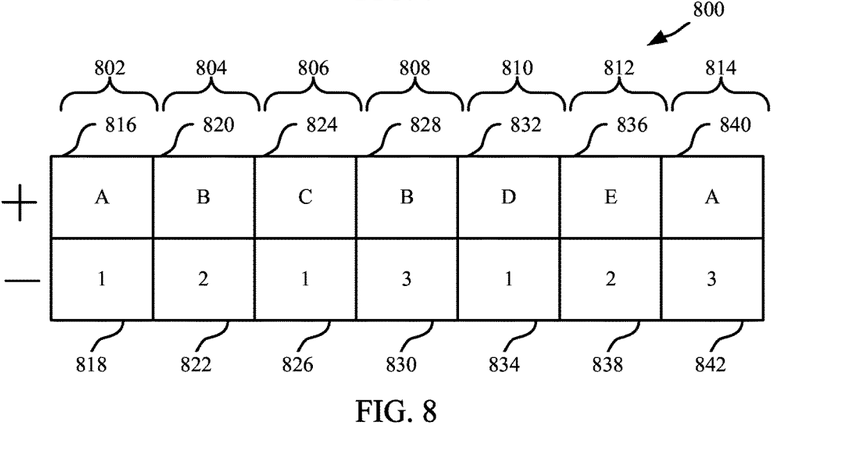
FIG. 8 is a schematic diagram of an ablation structure with seven electrode zones in accordance with various embodiments.

Turning to FIG. 8, a schematic diagram of an ablation structure 800 with seven electrode zones is shown in accordance with various embodiments. Ablation structure 800 may be another example of the ablation structure 700 described with reference to FIG. 7. As shown in FIG. 8, each of the possible adjacent-zone channel pairs of the ablation structure 800 (i.e., A2, B1, C2, C3, D3, E1, D2, and E3) are each electrically distinct from all of the in-zone channel pairs (i.e., A1, B2, C1, B3, D1, E2 and A3). Although the ablation structures 700 and 800 are depicted with seven electrode zones, it may be appreciated that the method of arrangement just described may be employed with an ablation structure with any number of electrode zones.

According to various embodiments, the electrode zones are longitudinal rectangular zones. However, the electrode zones may comprise any suitable shape such as square, oval, or circular. Moreover, all of the electrode zones may be the same size or shape, or an ablation device may comprise some electrode zones of one size or shape and some electrode zones of a different size or shape. For example, the longitudinal rectangular zones may all be equal in width and height, or some of the electrode zones may comprise a different width than other electrode zones. The plurality of electrode zones may be arranged adjacent to each other along a linear row as depicted in FIGS. 1-8. Furthermore, the ablation structure may include a single row of electrode zones or may include multiple rows of equal or unequal length stacked atop one another.

In accordance with various embodiments, any of the ablation structures as described herein may be coupled with one or more additional components to make up an ablation system for ablating tissue within a body lumen. For example an ablation system may include an expansion member that may be coupled with a distal portion of a catheter. An ablation structure may be coupled with an ablation structure support that is wrapped around the expansion member such that expanding the expansion member may engage body lumens of varying sizes.

Figure 9:
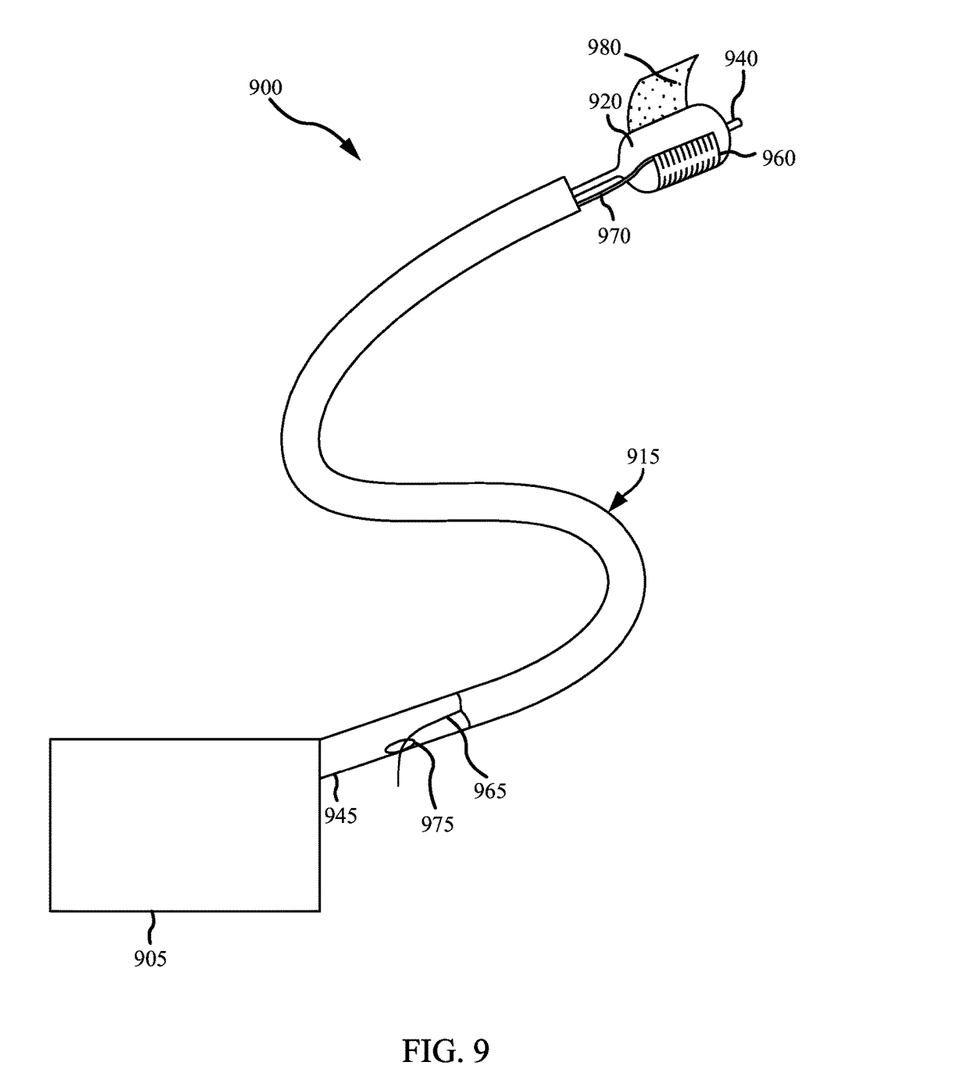
FIG. 9 is a schematic diagram of an ablation system for delivering treatment to a target treatment area including components configured in accordance with various embodiments.

With reference to FIG. 9, a general system 900 for delivering treatment to a target treatment area is shown in accordance with various embodiments. The system 900 may be designed for providing treatment to a target area inside of a body, such as the wall of an organ or lumens in the gastrointestinal tract, for example. The system 900 may include a power source 905, a catheter 915, and an expansion member 920. The expansion member 920 may generally be configured to support and ablation structure support 980 and an ablation structure 960 coupled with the ablation structure support 980. The ablation structure support 980 and ablation structure 960 may be furled at least partially around the outside circumference of the expansion member 920 such that when the expansion member 920 expands, the ablation structure support 980 adapts to the changing circumference while the ablation structure 960 maintains a constant electrode density per unit area. According to some embodiments, the ablation structure 960 and the ablation structure support 980 are configured to at least partially unfurl or furl around the expansion member 920 as the expansion member 920 expands or contracts. The feature of the ablation structure support 980 and ablation structure 960 furling and unfurling as the expansion member 920 expands and contracts is more fully described in co-owned U.S. application Ser. Nos. 14/519,409, 14/519,950, and 14/520,028, each of which are incorporated herein by reference for all purposes.

The system 900 may operate by positioning a guide assembly 965 inside a body and passing the expansion member 920 over the guide assembly 965 such that the expansion member 920 may be delivered to a target treatment site inside the body. The power source 905 may then be used to supply power to an ablation structure 960 disposed on the expansion member 920 so that therapy may be applied to the target treatment site. In accordance with various embodiments, the power source 905 may be configured to deliver non-grounded alternating current (AC) power to the ablation structure 960.

The expansion member 920 may be an inflatable device capable of transitioning between a collapsed or unexpanded configuration and an expanded configuration with the use of a supplementary expansion mechanism. Suitable expansion members 920 include but are not limited to a non-compliant balloon, a semi-compliant balloon, a compliant balloon, a balloon with a tapered geometry, a bladder, and the like. In some embodiments, the power source 905 is configured to inflate the expansion member 920 by, for example, incorporating the supplementary expansion mechanism internally. The collapsed configuration may be generally used when the expansion member 920 is inserted into and removed from the body lumen. When the expansion member 920 obtains a desired ablation position, the expansion member 920 may expand, such as by inflating from a deflated state (i.e., the collapsed configuration) to a substantially inflated state (i.e., the expanded configuration).

The expansion member 920 may be configured to support an ablation structure support 980. In some embodiments, the ablation structure support 980 includes a thin, rectangular sheet of polymer materials such as polyimide, polyester or other flexible thermoplastic or thermosetting polymer film. Moreover, the ablation structure 960 may be coupled with the ablation structure support 980. In some embodiments, the ablation structure 960 is a therapeutic or diagnostic instrument, such as an ablation element that may provide ablative energy to the target treatment area. The ablation structure 960 may be used to supply radio frequency (RE) energy to the target treatment site. Ablation structure 960 may be an example of any of the ablation structures 100, 200, 300, 400, 500, 600, 700, or 800 described with reference to any of FIGS. 1-8. Accordingly, the ablation structure 960 may include a plurality of discrete bipolar electrode zones.

The expansion member 920 may be coupled with the catheter 915 such that the expansion member 920 may be maneuvered through a channel of the body, such as the esophagus, and at the target treatment area. The catheter 915 may be coupled with the power source/inflation device 905 at the proximal end 945 of the catheter 915. The expansion member 920 may be positioned near the distal end 940 of the catheter 915. In some embodiments, the catheter 915 includes an opening 975 configured to allow the entry and exit of the guide assembly 965 such that the catheter 915 is slidably movable relative to the guide assembly 965. The guide assembly entry point 975 may typically be located outside of the catheter 915 and proximate the power source 905.

The power source 905 may provide power to the ablation structure 960 disposed on the expansion member 920. In some embodiments, power is provided from the power source 905 to the ablation structure 960 via one or more transmission lines 970 extending between the power source 905 and the ablation structure 960 and housed within a channel of the catheter 915. The transmission lines 970 may be examples of the distinct electrical channels as described with reference to FIGS. 1-8. For example, the transmission lines 970 may be distinct electrical wires. In some embodiments, the power source 905 is configured to selectively activate one or more of the plurality of electrode zones by selectively activating one or more of the distinct electrical channels. The feature of the power source 905 selectively activating particular channels of an ablation device and the associated circuitry is more fully described in co-owned U.S. application Ser. Nos. 14/519,409, 14/519,950, and 14/520,028, each of which are incorporated herein by reference for all purposes.

Figure 10:
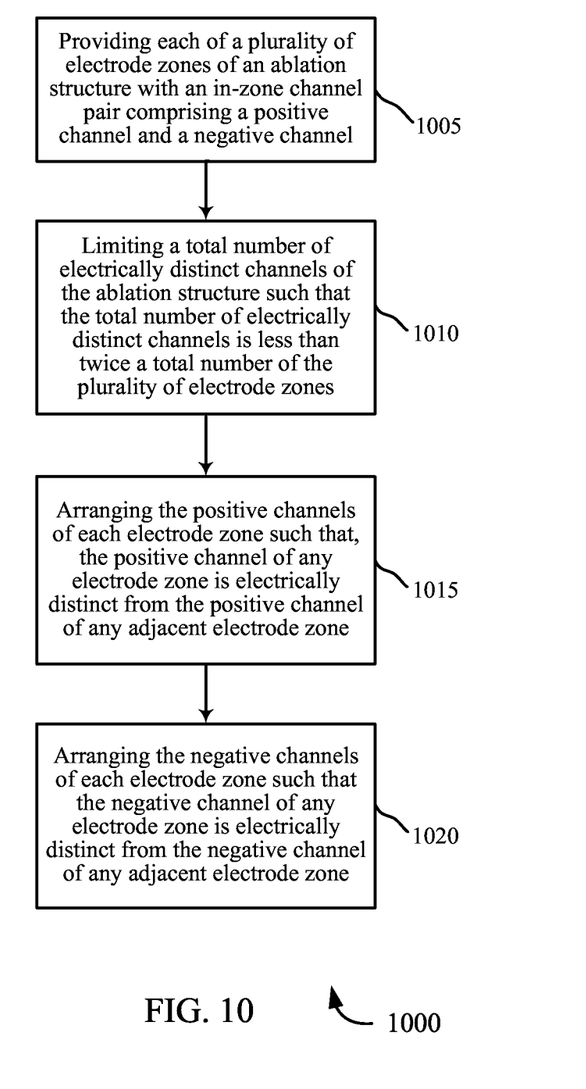
FIG. 10 is a flow diagram of a method for designing an ablation structure in accordance with various embodiments.

According to various embodiments, methods of designing a multi-zone ablation device are described. With reference to FIG. 10, a flow diagram of a method 1000 for designing an ablation structure comprising a plurality of electrode zones in accordance with various embodiments described herein is shown. The method may include at step 1005 providing each of the plurality of electrode zones with an in-zone channel pair comprising a positive channel and a negative channel. The method may further include at step 1010 limiting a total number of electrically distinct channels of the ablation structure such that the total number of electrically distinct channels is less than twice a total number of the plurality of electrode zones. Furthermore, at step 1015, the method 1000 may further include arranging the positive channels of each electrode zone such that, the positive channel of any electrode zone is electrically distinct from the positive channel of any adjacent electrode zone. At step 1020, the method 1000 may further include arranging the negative channels of each electrode zone such that the negative channel of any electrode zone is electrically distinct from the negative channel of any adjacent electrode zone.

The ablation structures 100, 200, 300, 400, 500, 600, 700, and 800 are examples of ablation structures designed in accordance with method 1000. However, it may be appreciated that method 1000 may be employed to design multi-zone ablation structures other than the embodiments illustrated in FIGS. 1-8. In particular, method 1000 may be employed to design ablation structures with any number of electrode zones and electrically distinct channels. Moreover, as described more fully below, method 1000 may be employed either alone or in combination with other steps to design a multi-zone ablation structure.

Figure 11:
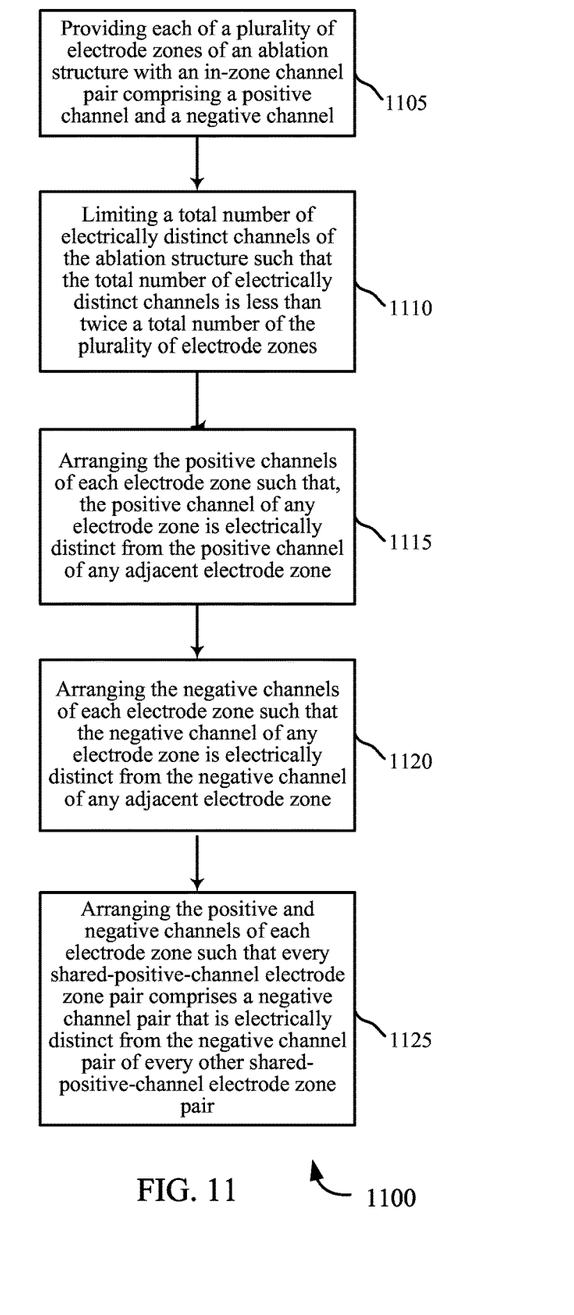
FIG. 11 is a flow diagram of a method for designing an ablation structure in accordance with various embodiments.

For example, with reference to FIG. 11, a flow diagram of a method 1100 for designing an ablation structure comprising a plurality of electrode zones in accordance with various embodiments described herein is shown. Steps 1105, 1110, 1115, and 1120 may be the same as steps 1005, 1010, 1015, and 1020 of method 1000. However, method 1100 may further include, at step 1125, arranging the positive and negative channels of each electrode zone such that every shared-positive-channel electrode zone pair comprises a negative channel pair that is electrically distinct from the negative channel pair of every other shared-positive-channel electrode zone pair.

The ablation structures 400, 500, 600, 700, and 800 are examples of ablation structures designed in accordance with method 1100. However, it may be appreciated that method 1100 may be employed to design multi-zone ablation structures other than the embodiments illustrated in FIGS. 4-8. In particular, method 1100 may be employed to design ablation structures with any number of electrode zones and electrically distinct channels. Moreover, it may be appreciated that the method described with reference to step 1125 may be employed either in combination with the steps of method 1000 (as described in method 1100), or step 1125 may be employed alone. For example, an ablation structure may be designed such that every shared-positive-channel electrode zone pair comprises a negative channel pair that is electrically distinct from the negative channel pair of every other shared-positive-channel electrode zone pair, but for at least one adjacent electrode zone pair, either the positive or negative channel between the zone pair is shared.

Figure 12:
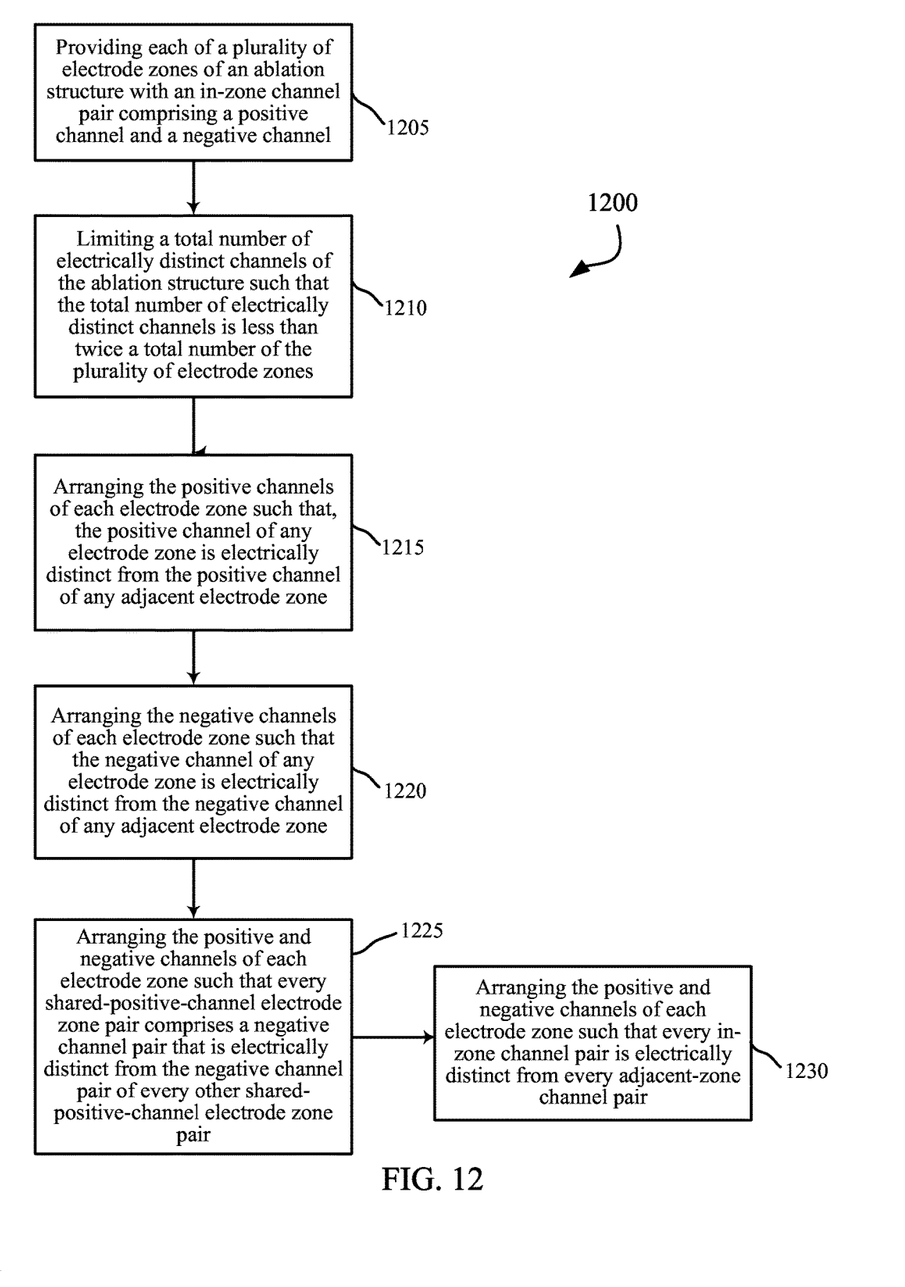
FIG. 12 is a flow diagram of a method for designing an ablation structure in accordance with various embodiments.

With reference to FIG. 12, a flow diagram of a method 1200 for designing an ablation structure comprising a plurality of electrode zones in accordance with various embodiments described herein is shown. Steps 1205, 1210, 1215, 1220, and 1225 may be the same as steps 1105, 1110, 1115, 1120, and 1125 of method 1100. However, method 1200 may further include, at step 1230, arranging the positive and negative channels of each electrode zone such that every in-zone channel pair is electrically distinct from every adjacent-zone channel pair. The ablation structures 700 and 800 are examples of ablation structures designed in accordance with method 1200. However, it may be appreciated that method 1200 may be employed to design multi-zone ablation structures other than the embodiments illustrated in FIGS. 7-8. In particular, method 1200 may be employed to design ablation structures with any number of electrode zones and electrically distinct channels.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

The invention claimed is:

1. An ablation device for treatment of tissue comprising:
an ablation structure comprising three or more bipolar electrode zones, each electrode zone comprising an in-zone channel pair comprising a positive channel and a negative channel,
wherein the ablation structure is configured such that, for any adjacent electrode zone pair comprising one electrode zone and another electrode zone adjacent to the one electrode zone, the positive channel of the one electrode zone is electrically distinct from the positive channel of the other electrode zone, and the negative channel of the one electrode zone is electrically distinct from the negative channel of the other electrode zone; and
wherein the ablation structure comprises a total number of electrically distinct channels that is less than twice a total number of the three or more bipolar electrode zones.

2. The ablation device of claim 1, wherein the ablation structure further comprises a plurality of shared-positive-channel electrode zone pairs, wherein each shared-positive-channel electrode zone pair of the plurality of shared-positive-channel electrode zone pairs comprises a negative channel pair that is electrically distinct from the negative channel pair of every other shared-positive-channel electrode zone pair of the plurality of shared-positive-channel electrode zone pairs.

3. The ablation device of claim 2, wherein the ablation structure is further configured such that every in-zone channel pair is electrically distinct from every adjacent-zone channel pair.

4. The ablation device of claim 1, wherein the ablation structure is further configured such that each electrode zone comprises an in-zone channel pair that is electrically distinct from the in-zone channel pair of every other electrode zone.

5. The ablation device of claim 1, wherein each electrode zone is configured to be selectively enabled or disabled.

6. The ablation device of claim 5, wherein each electrode zone is configured to be selectively enabled by supplying alternating current to the in-zone channel pair of each electrode zone.

7. The ablation device of claim 1, wherein the three or more bipolar electrode zones are aligned adjacent to each other.

8. The ablation device of claim 1, wherein the three or more bipolar electrode zones are all equal in width.

9. The ablation device of claim 1, further comprising:
a catheter;
an expansion member coupled with a distal portion of the catheter;
an ablation structure support coupled with the ablation structure, wherein the ablation structure and the ablation structure support are configured to at least partially unfurl or furl around the expansion member as the expansion member expands or contracts.

10. The ablation device of claim 9, wherein the expansion member comprises a balloon.

11. The ablation device of claim 10, wherein the balloon comprises a semi-compliant material.

12. The ablation device of claim 2, wherein the three or more electrode zones comprise six electrode zones, and wherein:
a first electrode zone of the six electrode zones comprises an in-zone channel pair comprising a first positive channel and a first negative channel;
a second electrode zone of the six electrode zones adjacent to the first electrode zone comprises an in-zone channel pair comprising a second positive channel and a second negative channel, wherein the first electrode zone and the second electrode zone comprise a first adjacent electrode zone pair;
a third electrode zone of the six electrode zones adjacent to the second electrode zone comprises an in-zone channel pair comprising a third positive channel and a third negative channel, wherein the second electrode zone and the third electrode zone comprise a second adjacent electrode zone pair;

a fourth electrode zone of the six electrode zones adjacent to the third electrode zone comprises an in-zone channel pair comprising the first positive channel and the fourth negative channel, wherein the third electrode zone and the fourth electrode zone comprise a third adjacent electrode zone pair;

and a fifth electrode zone of the six electrode zones adjacent to the fourth electrode zone comprises an in-zone channel pair comprising the third positive channel and the first negative channel, wherein the fourth electrode zone and the fifth electrode zone comprise a fourth adjacent electrode zone pair; and a sixth electrode zone of the six electrode zones adjacent to the fifth electrode zone comprises an in-zone channel pair comprising the second positive channel and the third negative channel, wherein the fifth electrode zone and the sixth electrode zone comprise a fifth adjacent electrode zone pair.

13. The ablation device of claim 2, wherein the three or more electrode zones comprise six electrode zones, and wherein:

a first electrode zone of the six electrode zones comprises an in-zone channel pair comprising a first positive channel and a first negative channel;

a second electrode zone of the six electrode zones adjacent to the first electrode zone comprises an in-zone channel pair comprising a second positive channel and a second negative channel, wherein the first electrode zone and the second electrode zone comprise a first adjacent electrode zone pair;

a third electrode zone of the six electrode zones adjacent to the second electrode zone comprises an in-zone channel pair comprising a third positive channel and a third negative channel, wherein the second electrode zone and the third electrode zone comprise a second adjacent electrode zone pair;

a fourth electrode zone of the six electrode zones adjacent to the third electrode zone comprises an in-zone channel pair comprising the first positive channel and a fourth negative channel, wherein the third electrode zone and the fourth electrode zone comprise a third adjacent electrode zone pair;

and a fifth electrode zone of the six electrode zones adjacent to the fourth electrode zone comprises an in-zone channel pair comprising the second positive channel and the third negative channel, wherein the fourth electrode zone and the fifth electrode zone comprise a fourth adjacent electrode zone pair; and a sixth electrode zone of the six electrode zones adjacent to the fifth electrode zone comprises an in-zone channel pair comprising the third positive channel and the fourth negative channel, wherein the fifth electrode zone and the sixth electrode zone comprise a fifth adjacent electrode zone pair.

14. The ablation device of claim 3, wherein the three or more electrode zones comprise seven electrode zones, and wherein:

a first electrode zone of the seven electrode zones comprises an in-zone channel pair comprising a first positive channel and a first negative channel;

a second electrode zone of the seven electrode zones adjacent to the first electrode zone comprises an in-zone channel pair comprising a second positive channel and a second negative channel, wherein the first electrode zone and the second electrode zone comprise a first adjacent electrode zone pair;

a third electrode zone of the seven electrode zones adjacent to the second electrode zone comprises an in-zone channel pair comprising a third positive channel and the first negative channel, wherein the second electrode zone and the third electrode zone comprise a second adjacent electrode zone pair;

a fourth electrode zone of the seven electrode zones adjacent to the third electrode zone comprises an in-zone channel pair comprising the second positive channel and a third negative channel, wherein the third electrode zone and the fourth electrode zone comprise a third adjacent electrode zone pair;

a fifth electrode zone of the seven electrode zones adjacent to the fourth electrode zone comprises an in-zone channel pair comprising a fourth positive channel and the first negative channel, wherein the fourth electrode zone and the fifth electrode zone comprise a fourth adjacent electrode zone pair;

a sixth electrode zone of the seven electrode zones adjacent to the fifth electrode zone comprises an in-zone channel pair comprising a fifth positive channel and the second negative channel, wherein the fifth electrode zone and the sixth electrode zone comprise a fifth adjacent electrode zone pair; and a seventh electrode zone of the seven electrode zones adjacent to the sixth electrode zone comprises an in-zone channel pair comprising the first positive channel and the third negative channel, wherein the sixth electrode zone and the seventh electrode zone comprise a sixth adjacent electrode zone pair.

15. The ablation device of claim 3, wherein the three or more electrode zones comprise seven electrode zones, and wherein:

a first electrode zone of the seven electrode zones comprises an in-zone channel pair comprising a first positive channel and a first negative channel;

a second electrode zone of the seven electrode zones adjacent to the first electrode zone comprises an in-zone channel pair comprising a second positive channel and a second negative channel, wherein the first electrode zone and the second electrode zone comprise a first adjacent electrode zone pair;

a third electrode zone of the seven electrode zones adjacent to the second electrode zone comprises an in-zone channel pair comprising a third positive channel and the first negative channel, wherein the second electrode zone and the third electrode zone comprise a second adjacent electrode zone pair;

a fourth electrode zone of the seven electrode zones adjacent to the third electrode zone comprises an in-zone channel pair comprising the second positive channel and a third negative channel, wherein the third electrode zone and the fourth electrode zone comprise a third adjacent electrode zone pair;

a fifth electrode zone of the seven electrode zones adjacent to the fourth electrode zone comprises an in-zone channel pair comprising a fourth positive channel and the first negative channel, wherein the fourth electrode zone and the fifth electrode zone comprise a fourth adjacent electrode zone pair;

a sixth electrode zone of the seven electrode zones adjacent to the fifth electrode zone comprises an in-zone channel pair comprising a fifth positive channel and the third negative channel, wherein the fifth electrode zone and the sixth electrode zone comprise a fifth adjacent electrode zone pair; and a seventh electrode zone of the seven electrode zones adjacent to the sixth electrode zone comprises an in-zone channel pair comprising the fourth positive channel and the second negative channel, wherein the sixth electrode zone and the seventh electrode zone comprise a sixth adjacent electrode zone pair.

* * * * *